United States Patent
Fuller et al.

[11] Patent Number: 5,833,683
[45] Date of Patent: Nov. 10, 1998

[54] LATERALLY-EMITTING LASER MEDICAL DEVICE

[75] Inventors: Terry A. Fuller, Rydal; Mark DeStefano, Collegeville; Sean M. O'Connor, West Chester; Kenneth R. Cook, Blue Bell, all of Pa.

[73] Assignee: Surgical Laser Technologies, Inc., Oaks, Pa.

[21] Appl. No.: 585,665

[22] Filed: Jan. 12, 1996

[51] Int. Cl.$^6$ .................................................. A61B 17/36
[52] U.S. Cl. ................................................................ 606/17
[58] Field of Search .................................. 606/14, 15, 16, 606/17, 4, 5, 6, 2, 3; 607/88, 89

[56] References Cited

U.S. PATENT DOCUMENTS

| | | |
|---|---|---|
| 4,126,136 | 11/1978 | Auth et al. . |
| 4,209,017 | 6/1980 | Shaw . |
| 4,273,109 | 6/1981 | Enderby ................................... 128/6 |

(List continued on next page.)

FOREIGN PATENT DOCUMENTS

| | | | |
|---|---|---|---|
| 0 184 928 | 6/1986 | European Pat. Off. | .......... A61N 5/06 |
| 0 407 229 A2 | 1/1991 | European Pat. Off. | ........ A61B 17/36 |
| 2 702 662 | 3/1993 | France | .............. A61N 5/06 |
| 2826383 | 12/1979 | Germany | ....................... A61B 17/32 |
| 2828322 | 1/1980 | Germany | ....................... A61B 17/36 |
| 2832847 | 2/1980 | Germany | ....................... A61B 17/36 |
| 53-8792 | 1/1978 | Japan | .............................. A61B 17/32 |
| 57-103712 | 6/1982 | Japan | .............................. A61B 17/36 |
| 57-163253 | 10/1982 | Japan | .............................. A61N 5/10 |
| 57-182414 | 11/1982 | Japan | .............................. A61C 1/08 |
| 59-120147 | 7/1984 | Japan | .............................. A61B 17/36 |
| 60-37311 | 3/1985 | Japan | .............................. A61B 17/36 |
| 61-135649 | 6/1986 | Japan . | |
| 62-11820 | 1/1987 | Japan | .............................. G02B 23/26 |
| 716762 | 7/1987 | Japan . | |
| 62-155820 | 10/1987 | Japan | .............................. A61B 17/36 |
| 62-200310 | 12/1987 | Japan | .............................. A61B 17/36 |
| 63-150062 | 6/1988 | Japan | .............................. A61B 17/36 |
| 1618399 A1 | 1/1991 | U.S.S.R. | .......................... A61B 17/36 |
| WO 92/08427 | 11/1991 | WIPO | .............................. A61F 9/00 |
| WO 93/03678 | 8/1992 | WIPO | ............................ A61B 17/36 |

OTHER PUBLICATIONS

Frank, "*Neue Instruments und Sicherheitsuntersuchungen zuer Anwendung des Neodym–YAG Lasers*" 1. Verh–Ber. d. Dtsch. Ges. f.Laser–Medizin Zuchschwerdt Munich, Germany 1983.

Hashimoto, "*A Lateral Radiation Probe In YAG Laser Therapy*", abstract), 4th Congress of Japan Society for Laser Medicine, Nov. 30, 1983, Japan.

(List continued on next page.)

*Primary Examiner*—Jennifer Bahr
*Assistant Examiner*—Sonya Harris-Ogugua
*Attorney, Agent, or Firm*—Seidel, Gonda, Lavorgna & Monaco, PC

[57] ABSTRACT

A laser medical device for delivering energy to tissue to be treated. The device includes a laser energy transmitting conduit having a longitudinal axis, and has a proximal end for connection to a source of laser energy and a distal end from which laser energy transmitted by the conduit is emitted. A laser energy redirecting member is located adjacent the distal end of the conduit for redirecting the laser energy in a lateral direction with respect to the axis of the conduit, and a tissue contact member is provided adjacent the laser energy redirecting member. The tissue contact member has a transverse cross section of preselected shape and a longitudinal axis generally transverse to the axis of the conduit. The tissue contact member further has an input surface for receiving laser energy redirected by the laser energy redirecting member and transmitting the laser energy received from the laser energy redirecting member. The tissue contact member terminates in a tissue contact surface having a radius of curvature. The dimensions of the tissue contact member and the radius of curvature of the tissue contact surface are determined and structural such that laser energy is transmitted divergently therethrough and impinges upon the tissue contact surface in a substantially diffuse pattern.

13 Claims, 5 Drawing Sheets

U.S. PATENT DOCUMENTS

| | | |
|---|---|---|
| 4,273,127 | 6/1981 | Auth et al. . |
| 4,445,892 | 5/1984 | Hussein et al. ............... 604/101 |
| 4,559,942 | 12/1985 | Eisenberg . |
| 4,592,353 | 6/1986 | Daikuzono . |
| 4,608,980 | 9/1986 | Aihara . |
| 4,646,737 | 3/1987 | Hussein et al. . |
| 4,693,244 | 9/1987 | Daikuzono . |
| 4,694,828 | 9/1987 | Eichenbaru . |
| 4,699,463 | 10/1987 | D'Amelio et al. ............... 350/92 |
| 4,736,743 | 4/1988 | Daikuzono . |
| 4,740,047 | 4/1988 | Abe et al. ............... 350/96 |
| 4,760,840 | 8/1988 | Fournier, Jr. et al. . |
| 4,773,413 | 9/1988 | Hussein et al. . |
| 4,785,815 | 11/1988 | Cohen ............... 128/642 |
| 5,020,995 | 6/1991 | Levy ............... 433/215 |
| 5,078,711 | 7/1992 | Kakami et al. ............... 606/16 |
| 5,163,935 | 11/1992 | Black et al. ............... 606/17 |
| 5,190,538 | 3/1993 | Hussein et al. ............... 606/17 |
| 5,242,438 | 9/1993 | Saadatmanesh et al. ............... 606/15 |
| 5,292,320 | 3/1994 | Brown et al. ............... 606/15 |
| 5,366,456 | 11/1994 | Rink et al. ............... 606/16 |
| 5,370,649 | 12/1994 | Gardetto et al. ............... 606/17 |
| 5,380,317 | 1/1995 | Everett et al. ............... 606/15 |
| 5,380,318 | 1/1995 | Daikuzono ............... 606/16 |
| 5,403,308 | 4/1995 | Wood et al. ............... 606/17 |
| 5,428,699 | 5/1995 | Pon ............... 385/31 |
| 5,437,660 | 8/1995 | Johnson et al. ............... 606/15 |
| 5,476,461 | 12/1995 | Cho et al. ............... 606/15 |
| 5,487,740 | 1/1996 | Sulek et al. ............... 606/15 |
| 5,496,307 | 3/1996 | Daikuzono ............... 606/15 |
| 5,496,309 | 3/1996 | Saadat et al. ............... 606/15 |
| 5,509,917 | 4/1996 | Cecchetti et al. ............... 606/15 |
| 5,562,657 | 8/1996 | Griffin ............... 606/17 |
| 5,571,099 | 11/1996 | Purcell, Jr. et al. ............... 606/17 |
| 5,593,404 | 1/1997 | Costello et al. ............... 606/15 |
| B1 4,592,353 | 4/1989 | Daikuzono . |

OTHER PUBLICATIONS

Hashimoto, *"Lateral Radiation Probe In YAG Laser Therapy"*, The Journal of Japan Society for Laser Medicine, 1984:4:1:153–154.

Hashimotyo, *"The Development Of Lateral Radiation Probes"*, Gastrointestinal Endoscopy, 1987:33:240–243.

Hofstetter et al., *"Lokale Laser–Bestrahlung Eines Peniskarzinoms"* (Treatment of penis carcinoma by laser), Urol. Klin. Univ. Munchen, Fortschr. Med. 1978, 96/8 (369–371).

Hofstetter et al., *"Ein Neues Laser–Endoskop Zur Bestrahlunf Von Blasentumoren"* (A novel laser endoscope for radiation of bladder tumors), Urol. Klin. Stad. Krankenh. Thalkirchner Strasse, Munchen, Fortschr. Med., 1979, 97/6 (232–234).

Surgical Laser Technologies, Inc., *"Side–Firing Free–Beam Probe (SFB 1.0),"* Surgical Laser Technologies, Inc., Oaks, PA (1994).

Hashimoto, *"Trial On Endoscopic Holography By Use Of Double Pulsed Laser"*, The Journal of Japan Society For Laser Medicine, 1984:4:1:47–48.

Hashimoto, *"Intra–Tumor Radiation Therapy By YAG For Deep Latent Lesions Under Ultrasonice Imaging"*, The Journal of Japan Society For Laser Medicine, 1984:4:1:171–172.

LATERALLY-EMITTING LASER MEDICAL DEVICE

FIELD OF THE INVENTION

The present invention relates to laser medical devices for use in medicine and surgery in which a probe conveys energy to tissue to be treated by the device. As used herein, the term "treated" means exposed to therapeutic energy, including but not limited to laser, thermal, or mechanical energy, for therapeutic procedures including but not limited to phototherapy, biostimulation, incision, vaporization (including without limitation ablation), coagulation (including without limitation hemostasis), and the like. In particular, the invention relates to a contact device which directs energy laterally through and out of a contact member which extends outward at substantially transverse angles to the longitudinal axis of the device.

BACKGROUND OF THE INVENTION

In many surgical procedures, a surgeon will use a surgical device to treat tissue by means of a pushing or pulling motion across or into the tissue. In other cases, the device may be moved downward onto the tissue, as when a surgeon depresses a scalpel into tissue. Surgical laser devices have been used thus in surgical procedures.

Surgical laser devices or systems supply energy from a laser source, through such energy delivery systems as fiber optic delivery systems or waveguides like articulated arms, to the tissue. In a number of cases, a probe is connected to the distal end of the energy delivery system to facilitate the delivery of therapeutic energy to the tissue being treated. From a general perspective, surgical laser devices or systems may be divided into categories: those that are designed for use not in contact with tissue, and those that are designed for use in contact with tissue. In these contexts, the term "contact" is understood to connote an optical element that transmits laser energy onto the tissue and that is intended to be used in contact with tissue.

Laser devices or systems that have been designed for use not in contact with tissue are the so-called free-beam systems. They typically emit the laser energy from the energy delivery system, through typically an air or liquid medium, to impinge directly upon the tissue to be treated. The tissue so impinged absorbs the laser energy according to various parameters; the relevant parameters will determine a temperature gradient created in the tissue in response to the laser energy. The resulting temperature gradient will dictate the sort of surgical lesion that results. Such non-contact systems can be designed to use a variety of mechanisms to alter the intensity, shape and direction of the laser beam irradiating the tissue. Use of such devices, however, can yield variable results because, among other things, the spot size of the laser beam upon the tissue can vary widely due to movements in the surgeon's hand or the patient's tissue. Discussed below are a number of surgical laser devices that radiate the laser energy onto the tissue in a direction lateral to the longitudinal axis formed by the energy at the Nd:YAG wavelength of 1,064 nanometers in order to coagulate the tissue to be treated, have lately been dubbed "side-firing" laser delivery systems or probes.

Other laser devices or systems have been designed for use in contact with tissue. In some cases, a probe is affixed to the laser energy delivery system, which is often a fiber optic cable. Such probes offer a number of advantages over free-beam energy delivery systems: they significantly reduce the waste arising from the backscatter of laser energy from the tissue; they define a clear and precise area of irradiation; they protect the optical fiber or other energy delivery system from fouling; and they provide tactile feedback to the surgeon. Perhaps most important, however, the probe may be treated to absorb or scatter laser energy, or both, such that both radiated photonic energy and conducted thermal energy can be delivered to the tissue. By varying the relative proportions of photonic and thermal energy, different temperature gradients, and resulting surgical lesions, can be created in the tissue. All of these contact devices have largely been designed to be used with generally dragging motions upon the tissue when used in open surgery. Such probes must have sufficient physical integrity, whether through material composition or corporeal mass, to withstand the mechanical and thermal rigors of surgery; without such integrity, they will cease to provide precise areas of irradiation. Discussed below are a number of laser probes that have been designed for use in contact with tissue.

In other cases involving devices or systems designed for use in contact with tissue, a discrete contact probe is not connected to the energy delivery system; instead, the energy delivery system itself is brought into direct contact with tissue. In still other cases, the distal end of the fiber optic cable can be configured to mimic the structure or function of a discrete probe. Generally, such configured fiber optics have yielded poorer results, for often tissue debris will form on the contact surface of the distal end of the fiber and cause it to deform and degrade, and thus the surgeon ceases to have a controlled and precise area of irradiation.

Many probes have been designed to direct the laser radiation in a direction generally parallel to or in line with the direction of the laser radiation that is emitted from the energy delivery system. There are, however, many surgical procedures where the tissue to be treated is inaccessible to laser radiation that follows such a path. A number of procedures call for laser radiation that is lateral, or sideways, to the direction of the radiation emitted from the energy delivery system. Those skilled in the art of laser surgical devices are familiar with the variety of means by which such lateral radiation may be produced at a surgical site.

One form of laser side-firing device is disclosed in U.S. Pat. No. 4,445,892, issued to Hany Hussein, et al. In that invention, a fiber optic cable delivers laser energy to a mirror placed in front of the fiber. The mirror is set at an angle that deflects the laser beam to a direction lateral to the longitudinal axis of the fiber optic. The mirror can be rotated around the distal end of the fiber optic, so that a wide arc of tissue can be irradiated from a single position of the fiber optic. The mirror and fiber optic are protected from contamination by surgical debris by means of a housing. The housing includes a transparent window through which the laser beam passes to the tissue or material (e.g., arterial plaque) to be treated. However, the device is to be used in a free-beam mode. It is not sufficiently robust to withstand contact with tissue that is being ablated and is not intended for such use. Since it is a free-beam device, it provides no tactile feedback. Moreover, it is suitable only for irradiation in a direction lateral to the fiber optic. Virtually no laser energy is radiated in a direction generally parallel to the longitudinal axis of the fiber optic.

Approaches similar to that in Hussein '892 are taught in Japanese patents 59-120147 and 60-37311. In these devices, however, the beam deflecting means is transparent to laser energy and draws in part upon principles summarized by Snell's Law to cause the laser beam to be deflected in a directional lateral to the direction of the fiber optic.

In another free-beam laser device, an optic fiber is beveled at its distal end such that the laser energy is reflected from the beveled distal surface and exits laterally from the fiber. The distal region of the optical fiber is encapsulated in a transparent glass ampule that presents a smooth, non-protruding face to the tissue being irradiated. Circon/ACMI has marketed such a device under the trademark UltraLine. The device is designed for free-beam use with Nd:YAG laser energy, and as such removes tissue by causing it to necrose and slough off over time. The device can be positioned in the various quadrants about the longitudinal axis of the fiber optic such that a circumambient arc of tissue about that axis may be irradiated. The ampule is designed to protect the fiber from becoming fouled with tissue debris. Such tissue debris will frequently collect on the ampule and cause it to become pocked and pitted, and, in some cases, to deform and break. The device is designed for a single surgical use.

In some cases, however, surgeons have applied the ampule of the UltraLine device directly to the tissue being treated, to mimic (albeit poorly) the structure and function of a standard, detachable contact probe. Surgeons have used the UltraLine in this manner in order to effect removal of the tissue by means of a technique called high power density vaporization. When used in contact with tissue, the ampule is even more prone to degrade and deform. The device can be so used in a backward and forward motion, but is not suitable or efficient for radial motion.

A different side-firing laser device is disclosed in U.S. Pat. No. 5,380,317, issued to Royice B. Everett et al. In this invention, an optical fiber delivers a laser energy beam to a so-called beam splitter found within a probe fitted onto the distal region of the fiber. Part of the beam is split and deflected at an angle lateral to the longitudinal axis of the fiber. The deflected part of the beam irradiates the tissue to be treated, passing free-beam through a distinctive trough-shaped aperture in the probe. The deflected laser radiation emitted from this device is intended to coagulate the tissue and cause it to necrose and slough off over time. The other portion of the beam is directed forward along the longitudinal axis of the fiber, and a forward sector of the probe absorbs this portion of the beam and converts it to thermal energy. The probe is to be held in contact with tissue so that the heat thus generated can be conducted to the tissue for therapeutic effect.

The device disclosed in the Everett '317 patent, however, is designed to have its primary surgical effect by virtue of the irradiative photonic effect, not the conductive thermal effect. The probe in that device is character bulbous, so as to allow a stand-off distance between the beam-deflector and the tissue. Insofar as the cavity that holds the distal end of the fiber optic in the probe is designed to be in communication with fluid from the surgical site, the distal end of the fiber optic and the so-called beam splitter and beam-deflector may become fouled, overheated and deformed.

The Everett '317 patent also discloses methods of laser surgery. The disclosed methods treat tissue by two modes: (1) laser energy is radiated laterally, free-beam to the tissue; and (2) thermal energy is conducted to the tissue as well. However, the tissue so irradiated is not the tissue that is at the same time in contact with the probe head and receiving the conducted thermal energy. In practice, the device is seldom used in contact with tissue.

Surgical Laser Technologies, Inc. ("SLT"), the assignee of the present invention, has marketed a side-firing, free-beam device similar to the invention disclosed in the Everett '317, yet different in that SLT's device is not bulbous and has no beam splitter. The side bore through which laser energy passes in SLT's device is cylindrical, and lacks the hallmark trough-shaped aperture of the invention in the Everett '317 patent. SLT's device also has a pressure-driven coaxially-supplied fluid coolant exiting the side bore so that fluid communicates only from the inside of the probe out, and not vice versa as in the invention in the '317 patent.

Building on the device disclosed in the Everett '317 patent is the invention disclosed in U.S. Pat. No. 5,437,660, issued to Douglas E. Johnson et al. In the Johnson '660 patent, a covering or operculum is set over the aperture through which the laser energy laterally exits the probe. The covering permits the laser energy to pass through it and into the tissue, but is designed to restrict the entry of tissue debris into the cavity where the beam splitter and beam-deflector are located. The characteristically bulbous shape of the probe ensures that the laterally-deflected laser beam passes through a gas or liquid medium before it reaches the tissue to be treated. The disclosed device is used solely to coagulate the tissue being treated.

The Johnson '660 patent teaches a method in which the device may be used. In each method, however, the temperature of the tissue is to be controlled below vaporization temperatures by means of irrigant that is supplied to the surgical site. Moreover, in each method, the surgeon is taught to select the positions from which the irradiation should take place and to predetermine the power level and duration at which the laser energy should be directed onto the tissue, and to predetermine the volume of irrigant to cool the surgical site. These predeterminations and selection are claimed to reduce the amount of time necessary for the surgery, and also to demand less skill and ex tempore judgment from the surgeon. Such predeterminations are rife in many previous applications of lasers.

Dental surgery has fostered some significant side-firing laser devices. In Japanese patent 53-8792, a side-firing delivery system is disclosed which concentrates the laser energy to a point by means of a converging lens. The concentrated energy can be used in free-beam mode on the tissue for small-area incision. Alternatively the laser beam can be channeled into a probe attachment that also physically converges.

Japanese patent 59-256136 discloses a side-firing laser device that has a spherical lens used in conjunction with the beam deflector and which also has a long, tapered probe through which the lateral beam passes. The patent teaches that if the very tip of the probe is dipped into carbon, the laser radiation exiting the distal portion of the conical probe is converted into thermal energy and is made more efficient in creating narrow incisions in tissue.

In Japanese patent 62-155820, several side-firing laser devices are disclosed. One such device is similar to the device in Japanese patent 59-256136. However, another such device has no conical probe attached to the side of the device. It merely has a spherical lens to concentrate the lateral beam to a point at or near the exit surface of the probe, such that the beam is diverging as it irradiates the tissue in a free-beam mode. Such divergent radiation is typically used for coagulation of the tissue to be treated. Having no protective covering for the beam deflector, the device is not suitable for use in contact with tissue.

The laser device disclosed in U.S. Pat. No. 5,020,995, issued to Guy Levy, is a free-beam, pulsed delivery system that can deliver laser radiation at a lateral angle to the surgical site. The patent teaches the use of the device in causing small, pit-like incisions in tooth tissue, depending significantly upon the different characteristics for absorbing laser radiation of the tissue to be treated and water present in the surgical field.

A different approach to laser surgery is disclosed in U.S. Pat. No. 4,773,413, issued to Hany Hussein et al. A portion of the laser energy is converted to thermal energy at the input surface of the probe. Another portion of the laser energy, effectively constituting the balance of the total laser energy, is allowed to pass through a central bore in the probe and thus irradiates the tissue directly. The Hussein '413 device has no disclosed means for causing the laser energy to irradiate the surgical site in a direction different from the path formed by the laser energy as it passes from the fiber optic (also sometimes referred to herein as an optical fiber) to the input surface of the laser probe. Moreover, in practice, the central bore becomes clogged with tissue debris. The debris in turn converts almost all the laser energy entering the bore into thermal energy, rendering the effect of the probe to be virtually the same as the effect of the probe disclosed in the related U.S. Pat. No. 4,646,737, issued to Hany Hussein et al.

U.S. Pat. No. 4,646,737 also teaches a surgical laser probe and a method for removing obstructions found in narrow lumens such as arteries. That method employs a laser probe with a distal-most heat generating element which receives the laser energy emitted from an optical fiber and absorbs and converts all the received laser energy into thermal energy. The heat generating element transmits no laser radiation to the tissue; instead, it builds up a store of heat and then is inserted into the material forming the obstruction in the tissue. Furthermore, the disclosed method is for softening, and creating a channel in, material causing an obstruction in a lumen, such as plaque obstructing an artery.

U.S. Pat. No. 4,209,017, issued to Robert F. Shaw, also teaches a method of laser surgery for a laser scalpel blade. Laser energy is transmitted through a transparent scalpel body to the cutting blade or edge. The laser energy is partially absorbed by a treatment in the blade region and thereby creates thermal energy that is conducted to the tissue being resected. The thermal energy provides hemostatis at the same time the mechanical force from the blade resects the tissue. Since no laser energy is irridiated into the tissue, the device is not a contact device, as intended herein.

U.S. Pat. No. 4,273,127 issued to David C. Auth, et al., teaches a method of laser surgery that depends upon a scalpel-shaped device that is transparent to laser energy. Laser radiation which is delivered through a fiber optic to the scalpel blade and which is emitted from the blade and the sides of the blade facilitates the mechanical cutting or parting of the tissue by the blade. If moved along the longitudinal axis of the fiber optic, the blade can effectively part tissue; however, if moved transversely to the longitudinal direction, the blade will be effective only in coagulating tissue.

SLT's own approach to laser surgery has depended upon approaches substantially disclosed in its U.S. Pat. Nos. 4,592,353, 4,693,244, and 4,736,743, issued to Norio Daikuzono. The Daikuzono '353 patent discloses laser probes that can be connected to an optical fiber and used in contact with tissue. The benefits of such probes are the reduction of backscatter associated with free-beam approaches, the ability to define a precise area of irradiation, the protection of the optical fiber from fouling, and the tactile feedback that is provided to the surgeon. The Daikuzono '244 patent provides the same benefits as a probe according to the '353 patent, and also defines an area of contact irradiation emitted by a frusto-conical tip end face that is suitable for incision of tissue. The Daikuzono '244 patent includes frusto-conical configurations fashioned directly upon the distal end of a fiber optic. The Daikuzono '743 patent discloses a treatment of the laser irradiation surface of laser probes used in contact with tissue such that a portion of the laser energy is converted to thermal energy. This latter patent effectively discloses how to achieve an effect similar to converting the wavelength of a portion of the laser energy of the laser source. When contact probes are used to vaporize tissue, they do so in the immediate course of surgery and therefore enable the surgeon to assess the adequacy of the surgical lesion on the spot. Unlike lesions that are created over time by necrosis and the sloughing off of tissue, the lesion created by an ablating contact probe can be immediately evaluated visually by the surgeon. SLT has marketed its probes under the trademark "CONTACT LASER."

The probes disclosed under the aforementioned three SLT patents have traditionally applied photonic and thermal energy to the tissue in a direction generally coaxial with the longitudinal axis of the fiber optic. As such, they can interfere with the surgeon's ability to view the results of the surgery as they unfold, if such view is endoscopic or coaxial with the energy delivery system. When used in a pushing motion, they can slip off the course the surgeon wants to make.

An outgrowth of the devices covered by the above three probes is disclosed in European Patent Application No. 90307486.2, assigned to SLT, for a laser catheter apparatus. A contact probe with a generally planar input surface is disclosed for irradiating tissue at an angle aligned with or offset from the longitudinal axis of the fiber optic. The disclosed probe may be used in a free-beam mode or in a contact mode using the teachings of the Daikuzono '743 patent. The orientation of the input surface and the shape of the output surface of the contact element of the probe determine how the beam will be deflected laterally. The output surface does not jut, or extend, beyond the exterior housing of the probe. The favored direction of this catheter is along the longitudinal axis of the fiber optic and the axis of the lumen being treated; where plaque is involved, the probe can be used to reform the plaque to conform to the walls of the lumen.

In Japanese design patent 716762, also issued to Norio Daikuzono but owned by SLT, a laser probe designed for use in contact with tissue is disclosed, which deflects the laser beam laterally. The laser beam passes through the probe and is reflected from a beveled distal face of the probe. The incident laser radiation is reflected at an angle to the side of the longitudinal axis of the fiber optic delivery system, instead of being refracted in a generally forward direction along with longitudinal axis. However, the contact surface of the probe, though rounded, does not protrude significantly beyond the exterior housing of the probe and therefore does not lend itself to improved visualization or for making wide swaths in the tissue from a stationary position of the fiber optic.

What is needed therefore is a device that can be used in contact with tissue so as to ablate broad areas of tissue which lie to the side of the longitudinal axis of the fiber optic; that can ablate such tissue smoothly and without forming ruts or grooves in the tissue or leaving significant vestiges or tags; that can be moved and can ablate easily not only in directions coaxial—whether forward or backward—with the longitudinal axis of the fiber optic, but also in sweeping, rotary, or transverse directions from the longitudinal axis; that can allow the surgeon to see the results of the surgery as they unfold; and that is structured such that it can readily slip down an endoscopic channel. Such a device will hew readily to the course that the surgeon wishes to make, and will reduce the time needed to conduct laser surgery. It will also reduce the intensity of the surgery by allowing the surgeon to concentrate more on the idiosyncrasies of the tissue being treated than on constraints imposed by the surgical instruments.

SUMMARY OF THE INVENTION

The present invention encompasses a laser medical device for delivering energy to tissue to be treated. The device comprises a laser energy transmitting conduit having a longitudinal axis and having a proximal end for connection to a source of laser energy and a distal end from which laser energy transmitted by the conduit is emitted, a laser energy erecting member adjacent the distal end of the conduit for redirecting the laser energy in a generally lateral direction with respect to the axis of the conduit, and a tissue contact member adjacent the laser energy redirecting member. The tissue contact member has a transverse cross section of preselected shape and a longitudinal axis generally transverse to the axis of the conduit. The tissue contact member further has an input surface for receiving laser energy redirected by the laser energy redirecting member and transmitting the laser energy received from the laser energy redirecting member. The tissue contact member terminates in a broad tissue contact surface having a general radius of curvature. The radius of curvature may, but need not, be infinite so as to encompass a flat surface. The dimensions of the tissue contact member and the radius of curvature of the tissue contact surface are determined and structural such that laser energy is transmitted divergently therethrough and impinges upon the tissue contact surface in a substantially diffuse pattern.

Preferably, although not necessarily, the invention is for use in wide-area vaporization or ablation of tissue. By the term "ablation" is meant the vaporization and removal of tissue over a broad area in the course of surgery. Ablation is to be distinguished from incision, which either simply parts tissue or else also removes tissue in a narrow and often deep field; and also from excision, which typically parts and removes diseased tissue en bloc from healthy tissue.

At the tissue contact surface of the tissue contact member, the laser energy may be in part converted to thermal energy and coupled as such into the tissue being treated, and in part coupled as laser radiation into the tissue being treated.

The tissue contact surface lies lateral to and outward from the laser energy transmitting conduit. In a preferred embodiment, the radius of curvature of the tissue contact surface is greater than half the average dimension of the cross-section of the contact member.

DESCRIPTION OF THE DRAWINGS

For the purpose of illustrating the invention, there is shown in the drawings a form which is presently preferred; it being understood, however, that this invention is not limited to the precise arrangements and instrumentalities shown.

DESCRIPTION OF THE INVENTION

Figure 1:
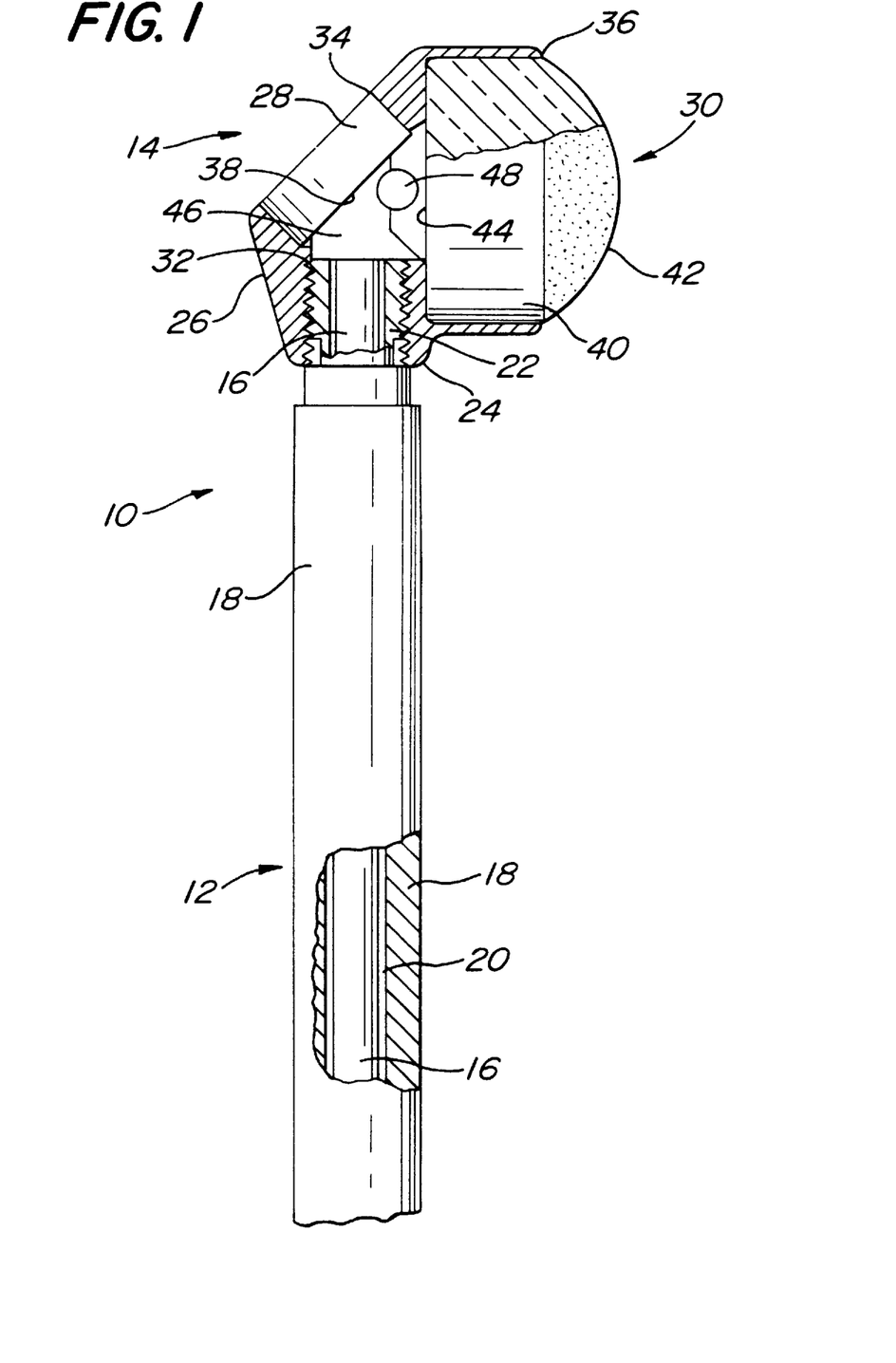
FIG. 1 is a side view, partially in section, of a laser energy delivery device including a transverse laser probe according to the present invention.

Referring now to the drawings, wherein like numerals indicate like elements, there is shown in FIG. 1 a laser energy delivery device 10 in accordance with the present invention. Device 10 comprises a laser energy transmitting conduit 12 and a tip member 14. (As used throughout this disclosure to describe the preferred embodiments of the invention, and as used in the claims, the term "member" is to be understood in its broadest sense, and includes not only discrete parts but also portions of an integral whole.) Laser energy transmitting conduit 12 comprises a flexible fiber optic 16 (usually also referred to herein as an optical fiber) contained within a flexible sheath 18. The optical fiber 16 is retained in sheath 18 and is substantially coaxial therewith, and the inner diameter of the sheath 18 is greater than the outer diameter of the optical fiber 16 so as to define an annular channel 20 between the inner diameter of sheath 18 and the outer diameter of optical fiber 16.

Although the energy transmitting conduit 12 is preferably a flexible fiber optic delivery system, other waveguides may be used if an optical fiber is not suitable. Where the energy transmitting conduit is a flexible fiber optic delivery system and is used in conjunction with a handpiece or endoscope, stiffeners may be added to the segment of the optical fiber that extends beyond the distal end of the handpiece or endoscope. Such stiffeners, often called wands, serve to maintain specific rigid paths for the fiber optic. Other stiffeners can be used without handpieces in order to maintain a semi-rigidity in the optical fiber. Semi-rigidity can be useful in keeping the therapeutic energy delivered by the invention in continuous contact with the tissue.

As shown in FIG. 1, the tip member 14 is mounted on what will be referred to herein as the distal end of laser energy transmitting conduit 12. The distal end of the optical fiber 16 may be provided with a connecting element that enables tip member 14 to be connected to optical fiber 16. Such a connecting element may, for example, be male/female threading used with a so-called universal connector, which is well suited to allow a tip member to be quickly removed and replaced in the course of a surgical procedure, and also to allow for removal of the tip member for cleaning and re-sterilization so that the tip member may be re-used. The opposite end (not shown) of laser energy transmitting conduit 12 will be referred to herein as the proximal end, which is adapted in any suitable, known manner for connection to a source of laser energy. Preferably, the source of laser energy is a continuous-wave (CW) source and not a pulsed source. The manner in which the proximal end of laser energy transmitting conduit 12 may be connected to a source of laser energy is known to those skilled in the art, and need not be described in detail herein. Any suitable manner of connecting the proximal end of conduit 12 may be employed without departing from or narrowing the scope of the present invention.

A portion of optical fiber 16 extends a short distance from sheath 18 at the distal end of conduit 12. The distal end of conduit 12 is provided with a fitting 22, which is generally tubular and is threaded on its outer surface. Fitting 22 may be attached to conduit 12 in any suitable manner, such as, by way of example and not limitation, via a universal connector known in the art. Fitting 22 has an inner diameter which is greater than the outer diameter of optical fiber 16. The portion of optical fiber 16 which extends from sheath 18 is received within the inner diameter of fitting 22. Since the inner diameter of fitting 22 is greater than the outer diameter of optical fiber 16, an annular channel 24 is defined around optical fiber 16. Channel 24 is in fluid-flow communication with channel 20, so that a suitable cooling fluid may optionally be supplied to tip member 14, as will be described in greater detail below.

Tip member 14 comprises a sleeve (sometimes called a housing) 26, a laser energy redirecting member 28, and a tissue contact member 30. Sleeve 26 holds the distal end of the optical fiber 16, the laser energy redirecting member 28 and the tissue contact member 30 in a fixed relationship and structure. It also protects these elements from contamination and degradation which could result from contact with tissue or debris in the surgical field. Sleeve 26 is preferably, although not necessarily, made of a surgical-grade stainless steel. Sleeve 26 can be provided with a tapped opening 32 for threadably receiving threaded fitting 22, so that sleeve 26 can be removably attached to the distal end of laser energy transmitting conduit 12. Sleeve 26 also includes a bore 34 at an angle to tapped opening 32. That is, the axis of tapped opening 32 and the axis of bore 34 intersect at an angle. Laser energy redirecting member 28 is fixedly mounted within bore 34. Preferably, the respective axes intersect at an angle such that the laser energy redirecting member 28 is preferably disposed at approximately a 45° angle with respect to optical fiber 16. However, angles ranging from approximately 25° to approximately 65° would be suitable for surgical applications. Sleeve 26 is further provided with a second bore 36 at preferably approximately a right angle to tapped opening 32, although angles between 25° and 65° could be suitable. Combinations of such angles are thus possible so as to permit irradiation in a lateral-to-retrograde direction. Tissue contact member 30 is fixedly mounted within second bore 36 such as, by way of examples and not limitation, using thermal compression or a mechanical clasp in an annular groove in the tissue contact member 30. It will be appreciated that the tissue contact member 30 will characteristically extend laterally or jut out from the longitudinal axis of the laser energy transmitting conduit 12 beyond the circumference of the laser energy transmitting conduit 12, and will also protrude from the sleeve 26. It is usual, but not necessary, that the tissue contact member 30 will be disposed at a right angle to the longitudinal axis of conduit 12, but it is within the scope of the invention that the tissue contact member be disposed at angles other than ninety degrees.

Laser energy redirecting member 28 is preferably a reflector. But the redirecting member may be also be a refractive prism without departing from the scope of the invention, and such prism may be a discrete element, an integral component of the tissue contact member, or an integral extension of the fiber optic. For convenience, the invention will be described herein with reference to a reflector, but it is understood that the example chosen to illustrate the invention in no way limits the invention to the particular example. Where the laser energy redirecting member 28 is a reflector, it is preferably a solid gold inset with a reflective inner surface 38. Gold is but one of many materials that are efficient reflectors of many forms of laser energy. The reflecting inner surface 38 should be of finish, composition, and dimensions that can withstand significant power of laser light, preferably over more than one surgical procedure. The laser energy redirecting member 28 is designed to redirect substantially all of the laser beam incident on it; only insignificant or unavoidable amounts of incident laser radiation should be absorbed by the laser energy redirecting member 28 and converted to heat. Such heat serves no therapeutic purpose, and can in fact be detrimental to the device. Optionally, but preferably, the device 10 is cooled to avoid such heat, as will be described more fully below.

The laser energy redirecting member 28 can also comprise elements transmissive to laser energy. Examples of such elements are prisms and lenses. Where transmissive elements are used, the deflection of the beam is primarily achieved with such materials by utilizing principles embodied in Snell's Law. Also in such cases, Fresnel losses will be encountered at each interface between one transmissive medium and another, and may generate within sleeve 26 heat having no therapeutic value. As already noted, device 10 is preferably cooled to avoid such heat, as will be described more fully below. When laser energy redirecting member 28 comprises a prism, it may be fused to the fiber optic 16 to avoid some Fresnel loss.

Tissue contact member 30 is preferably made of fused silica or quartz, although any other suitable material transparent to laser energy, such as, for example, sapphire, may be used. Suitable materials for tissue contact member 30 are familiar to those skilled in the art. Tissue contact member 30 comprises a generally cylindrical body portion 40 and a curved portion 42 which defines a tissue contact surface. It will be understood that while a curved surface having a finite radius of curvature is illustrated and described, it is within the scope of the invention for the radius of curvature of tissue contact surface 42 to be infinite, i.e., the tissue contact surface may be flat. Since the laser energy redirecting member 28 is located in front of the distal end of the optical fiber optic 16, laser radiation emitted divergently from the optical fiber 16 in a direction generally parallel to the longitudinal axis of the optical fiber will strike the laser energy redirecting member 28. Body portion 40 has an input face 44 which receives laser energy reflected from inner surface 38 of laser energy redirecting member 28, as will be described more fully hereinafter. Barring Fresnel losses, the laser energy is coupled into the tissue contact member via input face 44 and passes through to the tissue contact surface (curved portion 42) of the tissue contact member 30. Laser energy received at input face 44 is transmitted through body portion 40 and exits tissue contact member through the tissue contact surface of curved portion 42.

Tissue contact member 30, including body portion 40 and tissue contact surface 42, should have rounded or chamfered edges and joints so as to minimize drag that may result from sharp or angled edges. The body portion 40 and the tissue contact surface 42 likewise should not be of a shape or structure, such as, by way of example, cones or wedges, that tend by mechanical advantage to pierce or burrow into, and thus incise, tissue or, in addition, that fall outside a geometric envelope subtended by a curved surface having a radius of curvature equal to the maximum distance from the curved surface to the body portion 40, orthogonal to that surface.

Because of the characteristic lateral extension of tissue contact member from the longitudinal axis of the laser energy transmitting conduit 12, beyond the circumference of laser energy transmitting conduit 12, tissue contact surface 42 is spaced a preselected distance from the longitudinal axis of the laser energy transmitting conduit 12. It is desired that tissue contact surface not be flush with any portion of sleeve 26, but extend past sleeve 26 for some preselected distance.

Although tissue contact member 30 is described with reference to a particular example in which the body thereof is cylindrical, it should be understood that the invention is not so limited. Other shapes, such as those with elliptical or oval cross-sections, are within the scope of the present invention.

The curved tissue contact surface 42 of the tissue contact member 30 will typically have a generally convex, spherical surface and adjoin the body portion 40 such that no sharp edges or corners are created. Such a conformation facilitates smooth, multidirectional passage of device 10 onto and into the tissue to be treated without creating ruts or grooves in the tissue. However, conformations involving flat or even slightly concave, or ellipsoidal or other complex, curved surfaces, are also able to achieve substantially the same purpose and are to be understood to be encompassed by the present invention. A preferred curved surface is one that has a radius of curvature, or average radius of curvature for configurations which are not strictly spherical, that is not less than one-half the average dimension of the cross-section of the tissue contact member 30. Where the tissue contact member is substantially in the shape of a right circular cylinder, for example, the tissue contact surface has a radius of curvature not less that one-half the diameter of the cylinder.

The broad curved tissue contact surface 42 may be treated with infrared-absorbing materials such that a portion of the laser energy is absorbed and converted to heat. Exposure to radiated laser energy and conducted thermal energy from tissue contact member may 30 cause tissue contiguous to the curved tissue contact surface 42 to become so hot as to be vaporized or ablated. The infrared-absorbing materials may be set into the material of tissue contact member 30 or alternatively may be formed on the surface thereof. To enhance the bond between the infrared-absorbing materials and the material of tissue contact member 30, the material of the tissue contact member may be roughened so as to provide interstices in which the infrared-absorbing material may lodge. The infrared-absorbing materials may then be affixed to the surface of tissue contact member by adhesion, adsorption, or fusion into a matrix that may be molten into, or fused onto, the contact surface, or both.

Heat may be generated by tissue contact member 30 by other means as well, as for example microvacuoles within the material of the tissue contact member. Microvacuoles increase the temperature of the tissue contact member 30 by increasing the path length of the laser energy transmitted through it and by increasing thereby the amount of laser energy that is absorbed by the tissue contact member and converted to thermal energy.

It should be understood that it may happen in the dynamic context of laser surgery that an untreated segment of body portion 40 of tissue contact member 30 may come into contact with tissue, and may aid in the parting and ablation of the tissue. Consequently, body portion 40 can be used in a manner, and have a function and result, that are similar or practically equivalent to that of the curved tissue contact surface 42 of the contact element. It may, therefore, in certain cases be advantageous to treat a segment or portion of body portion 40 with infrared-absorbing material, particularly if a lesion which is to be deep as well as broad is desired from a pass of the probe against tissue.

It will be appreciated from FIG. 1 that, in the particular embodiment illustrated in the figure, the distal end of optical fiber 16, the inner surface 38 of laser energy redirecting member 28, and the input face 44 of tissue contact member 30 define an internal cavity 46 within sleeve 26. Internal cavity 46 is in fluid communication with channel 24 in fitting 22, and thus also in fluid communication through channel 24 with channel 20 in sheath 18. Thus, a suitable cooling fluid, such as a saline solution, can be supplied from a source of cooling fluid (not shown) to cavity 46 to prevent excessive heat buildup within tip member 14 during use. Cooling fluid can simply be carried away from the fiber-probe interface, or can be recirculated, in which case channels 20 and 24 would be divided, such as by an internal septum, into a supply channel and a return channel, or can be permitted to flow out of cavity 46 through a suitable orifice such as opening 48 through the wall of sleeve 26. Although the primary purposes of cooling fluid are to prevent excessive heat buildup within tip member 14 and ward off debris from the fiber/tip member interface, allowing the coolant to flow out of the tip member can also provide the effect of irrigating the surgical site, which may be beneficial in flushing debris from the surgical site. In most cases, allowing the coolant fluid to flow out of tip member 14 simplifies construction and fabrication of device 10, but recirculating the cooling fluid is within the scope of the present invention.

If desired, a guide wire (not shown) may be threaded through a separate channel in the sheath 18 and used to guide the device through body lumens.

Figure 2A:
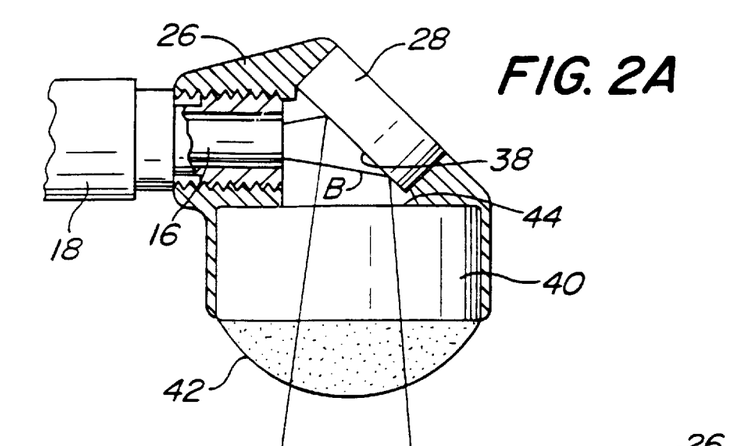
FIGS. 2A through 2C are schematic representations showing the energy distribution of three different embodiments of the probe of FIG. 1.

The laser energy distribution pattern, or beam profile, of the device 10 is illustrated schematically in FIG. 2A. The embodiment of the invention illustrated in FIG. 2A employs a laser energy redirecting member 28 having a planar inner surface 38, substantially as previously described. Tissue contact member 30 is also substantially as previously described, and has a planar input face 44. The laser energy transmitted down optical fiber 16 from a source of laser energy exits the fiber in a divergent beam, designated in the figure by reference character B. The beam strikes surface 38 of member 28 and, because of the angle between the axis of the optical fiber 16 and the plane of surface 38, is reflected in a divergent manner. The beam then enters tissue contact member 30 through planar input face 44. The beam is refracted slightly as it enters tissue contact member 30 because the index of refraction of tissue contact member 30 is greater than that of the surrounding medium, and propagates through tissue contact member 30 until it reaches curved tissue contact surface 42.

It will be appreciated that the laser energy diverges as it passes through tissue contact member 30 and does not couple out of the walls of body portion 40. Thus, the beam will typically propagate through body portion 40 without undergoing internal reflection. However, there may be situations in which such internal reflection is desired, and in those cases the dimensions and arrangement of the various elements of tip member 14 can be chosen to provide internal reflection. A deliberate occurrence of one internal reflection may help ensure that laser energy is emitted from the entire tissue contact surface 42 and even from distal portions of the walls of body portion, as will be described below.

From the tissue contact surface 42, the beam exits tissue contact member 30. As it exits, the beam again refracts slightly, since it typically enters a medium (i.e., tissue) having a lower index of refraction than tissue contact member 30.

It is possible to alter the profile and intensity of the laser beam as it passes out of the fiber optic and into the contact element, via the beam redirecting element. For example, referring to FIG. 2B, a laser energy redirecting member 280 is employed which, in contrast to member 28, has a convex inner surface 380. As beam B strikes convex surface 380, it diverges even more widely than it would if it were reflected from a planar surface. Consequently, the beam profile as it exits tissue contact surface is substantially more divergent in the embodiment shown in FIG. 2B than in the embodiment shown in FIG. 2A.

Figures 2B, 2C:
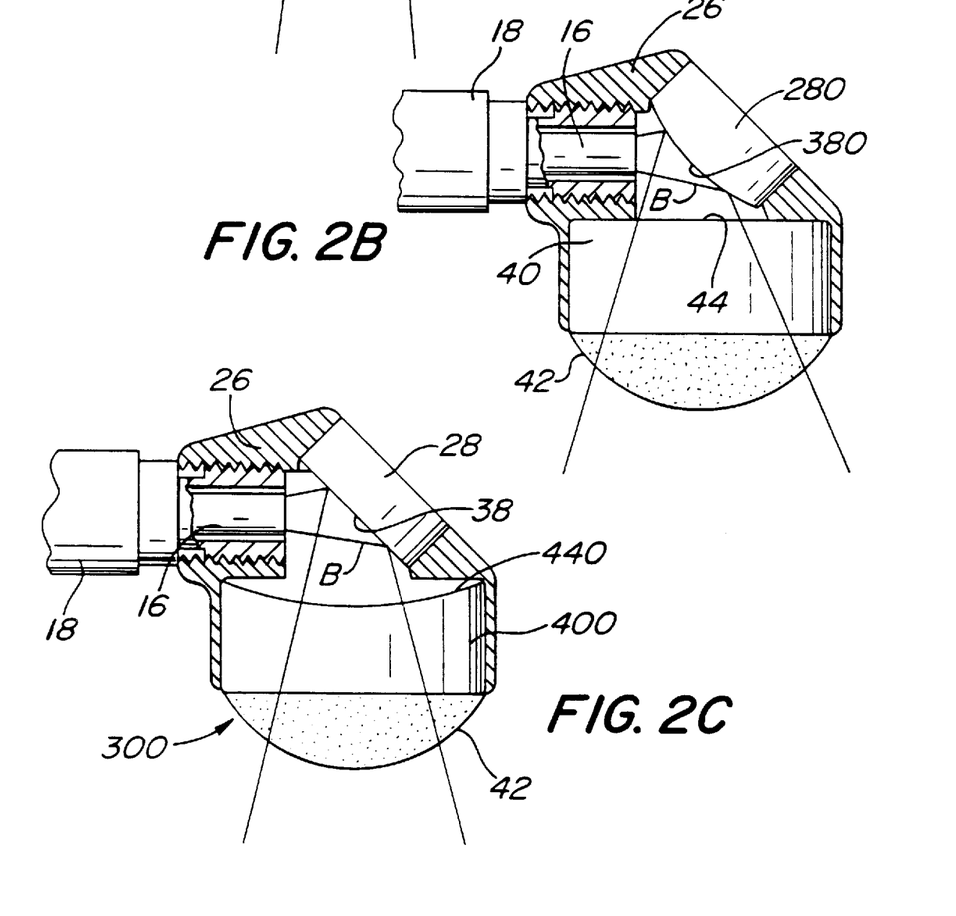

As another example, illustrated in FIG. 2C, it may be desirable to make the input surface of the tissue contact member concave, so that the beam's divergence is enhanced along its passage within the element to the distal contact surface. Broadening the divergence helps flatten the energy distribution of the beam profile exiting the contact surface from a commonly encountered semi-Gaussian output pattern. Thus, in FIG. 2C, the device has a tissue contact member in the form of a cylinder 400 with a concave input face 440. The laser energy redirecting member 28 is in the form of a reflector having a planar inner surface 38. Beam B is reflected divergently from surface 38 and, because input face 440 is concave, diverges even more when it enters tissue contact member 300.

In addition, various reflective, refractive, and scattering devices and materials may be set in the path of the beam to cause it to diverge, converge, collimate, or scatter. For example, it is possible to induce great diffusion of the laser beam by passing it through a transmissive medium that is filled with tiny microvacuoles. Such a medium, if of fused silica, may be abutted or integrated to other fused silica media such that no Fresnel losses are induced in passing from the one medium to the other.

Figure 3:
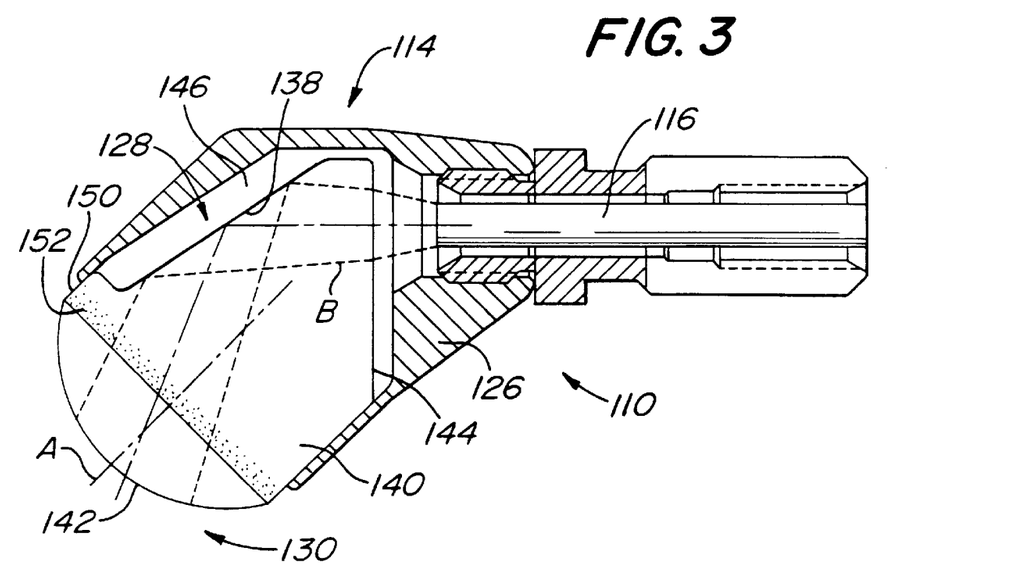
FIG. 3 illustrates a device according to another embodiment of the invention, wherein the probe operates on principles of internal reflection to laterally redirect laser energy.

FIG. 3 illustrates another embodiment 110 of the present invention, in which the tissue contact member is disposed at an angle other than 90° to the axis of the laser energy transmitting conduit and in which the tissue contact member integrally incorporates the laser energy redirecting member. In the embodiment illustrated in FIG. 3, tip member 114 comprises a sleeve 126 and an integral structure comprising a solid body of laser transmissive material and defining a laser energy redirecting member 128 and a tissue contact member 130. In this embodiment, laser energy redirecting member 128 is not a separate component such as reflector 28, but is integral with body portion 140 of tissue contact member 130. Laser energy, as schematically illustrated by beam B in the figure, emitted by the distal end of fiber optic 116 strikes input face 144 of tissue contact member 130 and is transmitted through it. The beam B strikes inner surface 138 of tissue contact member, where it is internally reflected and redirected in a direction generally toward tissue contact surface 142, from where it exits tissue contact member (or is optionally partially converted to thermal energy). Tissue contact member 130 is surrounded by an internal cavity 146 which may be occupied by air or which may, but need not, be fluid cooled.

It can be seen from FIG. 3 that tissue contact member 130 is disposed at an angle of other than 90° to the longitudinal axis of fiber optic 116. That is, tissue contact member has a longitudinal axis A which intersects the longitudinal axis of the fiber optic 116 at an angle other than 90°. As mentioned above, angles between about 25° and about 65° are suitable angles for surgical uses of the invention.

As those skilled in the art will understand, applying the principles of Snell's Law, laser energy striking inner surface 138 will not be emitted from laser energy redirecting member 128, but will be reflected from inner surface 138 at an oblique angle. The direction of the redirected beam B may or may not be coaxial with the longitudinal axis A of tissue contact member 130. The angle of the inner surface 138 relative to the longitudinal axis A will, at least in part, determine the direction of the redirected beam. As those skilled in the art will also understand, the direction of the redirected beam can be varied by varying the angles and dimensions of the tissue contact member, the contour of surface 138, and the angle at which input face 144 is disposed relative to the longitudinal axis of the fiber optic 116, without departing from the invention.

It is also within the scope of the invention that the tip member 14 or 114 can be fused directly to the output face of fiber optic 16 or 116, such that there is no gap between them. Also, the optical fiber could be cut to have an integral reflective surface, or a refractive element could be fused to the fiber optic, or a discrete refractive element could be used. Alternatively, any gap between the tip member and the output face of the fiber optic can be filled with a solid laser transmissive material. Preferably, the materials of the tip member, the fiber optic and any filler are all the same, so that there are no interfaces and, consequently, no Fresnel losses of the laser energy as it propagates from the fiber optic to the tissue contact surface of the tip member.

It was mentioned above that it may in certain cases be advantageous to treat a portion of the body portion of the tissue contact member with an infrared-absorbing material, such as, for example, where a deep lesion is desired. Such treatment is illustrated in FIG. 3, in which a circumferential segment or portion 150 of body portion 140 extends beyond the end of sleeve 126 immediately proximal to tissue contact surface 142 and is treated with an infrared-absorbing material (indicated in the figure by a stippled band 152). Such treatment may be in place of or, preferably, in addition to, similar treatment of tissue contact surface 142. Of course, an extending circumferential portion treated with an infrared-absorbing material may also be provided in the embodiments of the invention illustrated in FIGS. 1 and 2, without departing from the scope of the invention. As noted above, it may be desirable in these cases to intentionally cause the laser energy to undergo an internal reflection to ensure that laser energy is emitted from the entire tissue contact surface and from circumferential portion 150.

It is generally desirable, though by no means a requirement, that the laser energy be uniformly distributed over the contact surface. Such distribution can be abetted by such various means as placing diverging lenses in the path of the laser beam, shaping the beam receiving face of the contact element, disposing scattering materials in or on the contact element. Thus distributed, the laser energy can be converted to thermal energy uniformly in a desired proportion. If the laser energy is concentrated over a smaller surface area centered about the lateral axis or path of the laser energy as it is coupled into the tissue contact member, then the tissue contact surface has a tendency to bury itself deeply into the tissue. If a broader path is desired than the diverging beam from the laser energy redirecting member 28 can fill, it is possible to alter the contour of the reflecting surface or to interpose other lensing or scattering capabilities in the path of the beam in order to increase the divergence of the beam.

Figure 4:
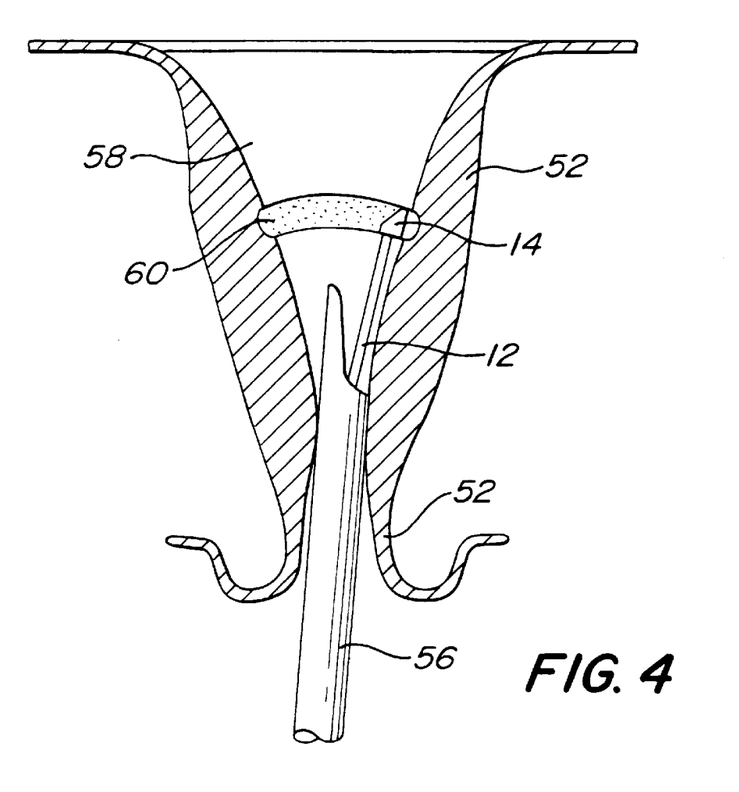
FIG. 4 illustrates a device according to the present invention as it might be used to perform ablation of tissue lining the uterus.

The device 10 according to the present invention lends itself well to the following uses. The device 10 can be used in a backward and forward direction in order to ablate tissue. Such movement, whether to and fro, or only in one of the two directions, is a use that comes naturally to the surgeon from use of other, conventional surgical instruments. The device 10 may be moved over the tissue in a direction that is transverse to the longitudinal axis of the energy delivery system. Procedures in open surgery usually have fewer constraints on the movements that the surgeon can make, so movements of the device 10 in line with or transverse to the longitudinal axis of the energy delivery system are generally possible. Successive passes of the tissue contact member can be made over and into the tissue. Light, continuous contact is sufficient to achieve the desired ablation; mechanical pressure of the device 10 against the tissue is not necessary. If crests and peaks of tissue should form, they may be removed by overlapping passes over the tissue. Given the structured balance in the contact surface between the radius of curvature and the longitudinal and radial dimensions of the tissue contact member 30, which define the breadth, depth, and contour of the contact surface, it is practicable to flatten and smooth such crests and peaks without slipping off them and falling back into the adjoining troughs. The device 10 can also be used in a sweeping motion. Such use is particularly favorable where the energy delivery system has less leeway for lateral movement than the device 10 and a more distal portion of the energy delivery system have for lateral movement. An example exhibiting such a constraint, illustrated in FIG. 4, would be a laser energy transmitting conduit 12 that passes into the uterus 52 through the uterine cervix 54, so that the device 10 may be used for ablation of the tissue lining the uterus (i.e., the endometrium). In that case, the laser energy transmitting conduit 12 is typically inserted by means of an endoscope 56 into the uterus 52. The tip member 14 can be swept in an arc over and on the endometrial tissue 58, where the endoscope can act as a pivot for the sweeping motion. This creates a swath 60 of ablated tissue.

The device 10 can further be used in a rotary or rotational motion. This use is favorable when the device 10 is to be used in a narrow lumen of the body and the tissue or material to be removed is found dispersed over the walls of the lumen. Removing adenoma resulting from benign prostatic hyperplasia is a use having such a characteristic. In very narrow lumens, the device 10 is also inserted by means of an endoscope, and may be repeatedly rotated or twisted clockwise and counterclockwise (or vice-versa) to achieve removal of substantial areas of tissue about a single position of the endoscope. As the lumen is made more patent, then the endoscope may itself be rotated within the lumen, so as to enable further radial ablation of the tissue or material.

A combination of such motions is possible. For example, a surgeon may use the device 10 of the present invention to create, by means of forward and/or backward movements, certain deep and narrow channels in tissue. See FIG. 5A at item 68. Such channels may be used, for example, to mark the bounds of the tissue to be removed or to create surgically-indicated channels or landmarks. The bounded tissue may be ablated by means of by similar backward and forward movements, or by transverse movements, or by swiveling or sweeping movements, as illustrated by items 74 and 76 in FIG. 5A. If removal in one direction leads to some residual undulation in the tissue, i.e., crests and peaks, then removal may be facilitated by moving the device 10 in a direction orthogonal to the direction of the initial movement, and at the same time rapidly swiveling or rotating clockwise and counterclockwise and so forth.

In all cases, the device 10 can be laid on the tissue somewhat on its side or tilted, such that the contact surface remains visible. See FIG. 5B. Because the contact surface is offset from longitudinal axis of the laser energy transmitting conduit 12, the surgeon can observe the progress of the ablation and also gain assurance that the contact surface of the device 10 is working within anatomical landmarks. Enhanced visibility leads to enhanced safety. Moreover, the device is not limited to ablation, and a surgeon may utilize the above techniques and motions in other tissue treatments.

The extension of tissue contact member 30 from the longitudinal axis of the laser energy transmitting conduit 12 enables the surgeon to observe the progress of the surgery better than when conventional contact probes are used, particularly in endoscopic procedures. When such conventional probes are used endoscopically, they are usually pushed forward onto the tissue, and seldom capable of being pulled back through the tissue with a therapeutic outcome. In each case, but even more so in the latter instance, the probe and the course of the lesion it creates are obscured by the energy delivery system. On the other hand, the tissue contact member 30 of the present invention is held at a slight angle to the longitudinal axis of the laser energy transmitting conduit 12. Held in this manner, the endoscope, or the energy delivery system in an open (non-endoscopic) procedure, does not prevent the surgeon from viewing the contact member. This is a significant advantage to a surgeon, for a surgeon is trained that it is necessary to know where the surgical lesion is initiated, where it progresses, and where it finishes. The course of the lesion is often gauged by anatomical landmarks. It is preferable that the surgeon should know the course of the lesion by direct observation of the course and the landmarks. The surgeon, for example, can better locate and stanch bleeding vessels. Extending the tissue contact member 30 from the longitudinal axis of the energy delivery system satisfies this surgical requirement for lesions which follow a course generally parallel to or in line with the longitudinal axis of the energy delivery system and which are formed by backward and/or forward movement of the device 10.

It is further desirable that the lateral extension of tissue contact member 30 be long enough that by canting the energy delivery system only slightly, the surgeon can obtain a clear view of the tissue contact surface 42 and the course of the lesion it makes. It is usually of less importance that the body portion 40 of the contact member be visible. In addition, the lateral extension, if neither too shallow nor too deep, aids in maintaining firm, continuous contact with the tissue. It has a tendency to keep the tissue contact member on the course the surgeon desires to make. The smaller the jut, the greater the cant, and the greater the cant, the less tissue removed in each pass. Too great a cant will drag the untreated portion of the body portion 40 into the tissue, and slow the procedure down. The amount of lateral extension will also be influenced by a need that may exist to be able to insert the device down an endoscope channel, as opposed to back-loading the device.

The lateral extension of the tissue contact member equally facilitates ablation or other treatment of tissue over a course which runs lateral to the longitudinal axis of the energy delivery system and which is formed by a transverse or sweeping movement of the device 10 with respect to the longitudinal axis or by rotational or swiveling movement of the device 10 about the longitudinal axis. The greater the extension, the greater the volume of tissue that may be ablated by radial movement of the device 10 about a single position of the energy delivery system. The tissue contact member thus can be moved multidirectionally. The surgical procedure will dictate the proper balance of movements.

It is also important that where the tissue contact member must ablate broad areas of tissue, it should not create ruts or grooves in the tissue. Frusto-conical contact probes with small-diameter tip end faces are designed for incision and are not well-adapted for ablation of broad areas of tissue. Such probes become buried in the tissue and create ruts and grooves, and when used to clean up the rises and crests between the troughs, the probes will often fall into one of the ruts or troughs to the side, forming thereby a deeper rut and failing to remove the rises and crests. Even some contact probes that present spherical contact surfaces to the tissue can create such ruts if they burrow into the tissue and form deep lesions, especially if they are used in a pushing motion in line with the longitudinal axis of the energy delivery system. Such ruts, along with other wisps and vestiges of tissue, called tags by some surgeons, will necrose and slough away over time. This delayed effect retards the healing process and, in the opinion of some surgeons, can lead to irritation and pain in the healing process. For these reasons, some surgeons prefer to leave a smooth, rut-free and tag-free surgical lesion. The present invention enables a surgeon to do this.

In order to avoid the formation of ruts, it is desirable that in each pass of the contact member, the member should not sink into the tissue so deeply that the depth of the tissue ablated by the untreated segment of the body portion 40 is as great as or greater than the greatest depth of the tissue ablated by the contact surface. It is also desirable that the contact surface be of sufficient breadth that it responds to the surface tension of the tissue as a means to avoid becoming deeply buried in the tissue. Thus, a tapered frusto-conical probe is designed to overcome the natural resistance of the tissue to thermal and mechanical penetration. If such a device were used first to create channels in the tissue along directions generally in line with the longitudinal axis of the energy delivery system, and then moved transversely to that axis in order to sweep away the peaks and ridges of tissue between the channels, the device will cross-hash and pock the tissue. Preferably, in the present invention the tissue contact surface 42 is gently curved so that successive, overlapping passes of the contact element will be able to smooth the treated surface of the tissue such that there is a generally uniform zone of coagulation free of ruts and tags, and therefore healing of the tissue progresses uniformly. Flat contact surfaces can serve well, too.

It is also desirable that the tissue contact surface 42 should be generally radially symmetric with respect to the lateral axis or path of the laser energy as it is coupled into the tissue contact member 30. Such symmetry enhances the ease of use of the device, for in whichever direction the surgeon moves the contact element, the therapeutic effect would be generally similar. Clearly, however, where certain specific directions are preferred, or where certain directions are to be avoided, then radial symmetry may be dropped in favor of more limited forms of symmetry, or even to asymmetry. Thus, in some surgical procedures, it may be preferred to establish ridges or humps in the contact surface so that upon either reciprocating or rotational motion, grooves or ridges that will not slough away, or that will slough away more slowly, can be made in the tissue.

In narrow lumenal work, there is concern that the heat generated in the forward region of the probe should not make the sides of the probe so hot that the lumenal walls could be damaged. The present invention obviates this concern by controlling the structure and placement of the sleeve and the laser-emission and heat-conversion patterns of the tissue contact surface as well as by optional coaxial coolant of the interface between the fiber optic and the tip member, where such interface exists.

Figure 5A:
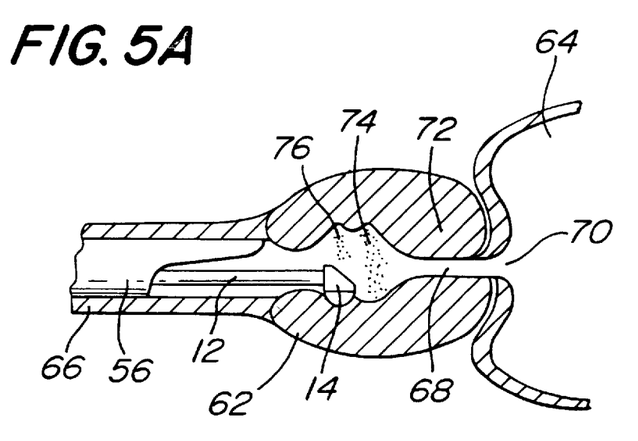
FIGS. 5A and 5B are schematic representations of a device according to the present invention as it might be used to perform a transurethral resection of the prostate.

In a preferred method of using the device 10, a surgeon would perform a transurethral resection of the prostate (TURP), also commonly called prostatectomy. See FIGS. 5A and 5B. FIG. 5A is a cross-sectional view through the prostate 62, also showing the bladder 64 and the urethra 66.

First, a bladder neck incision would be made with the same device 10, inserted through an endoscope 56. The incision would create a narrow ditch or channel 68 from the bottom (6 o'clock position) of the bladder orifice 70 and lead into the prostatic fossa 72. The cross-section of the channel measuring depth by breadth would be sufficient as to allow normal volumes of urine to be passed under normal outflow pressure.

Second, the device 10 of the present invention would ablate adenoma from the median lobe, starting at a point that is at the end of the channel. The laser would be set to deliver 40–50 watts of laser energy to the device 10. A transverse motion and/or a sweeping motion can be used to create a first swath 74 in the median lobe. Successive passes, and thus successive swaths such as second swatch 76, are made in this manner in antegrade directions, toward the veru montanum. The successive passes of the device are made so as to create overlapping swaths or swales of ablated tissue. If a ridge or gap is created between such swales, the device can be laid upon the ridge and can sweep the ridge away. Within a distance of about two passes from the veru, the transverse and sweeping motions will be stopped.

Third, the device 10 then is placed in the adjacent tissue lobes and proximal to the first transverse swath, and successive swaths made by transverse and sweeping motions are made, reducing the volume of tissue obstructing the fluid outflow. If peaks and troughs, or tags, form at any point in the procedure, the surgeon can simply move the device 10 over the non-conforming area in a direction opposite to the original direction and at the same time quickly swivel the device 10 clock and counterclockwise.

Figure 5B:
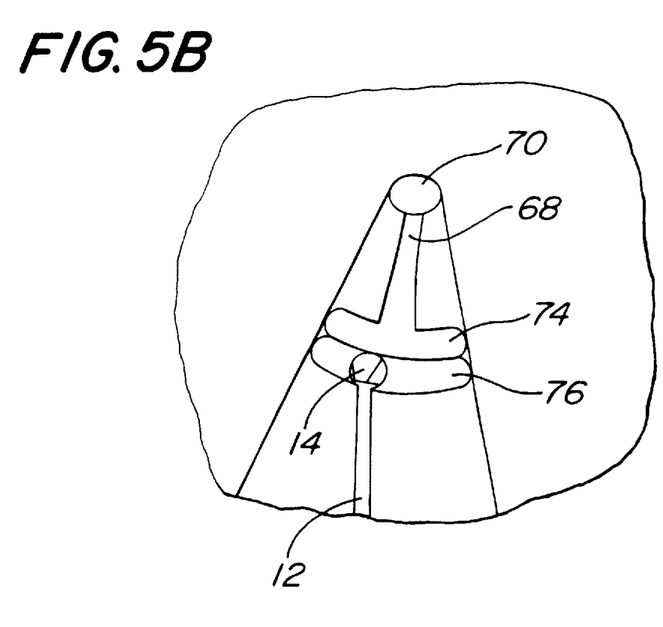
Figure 6:
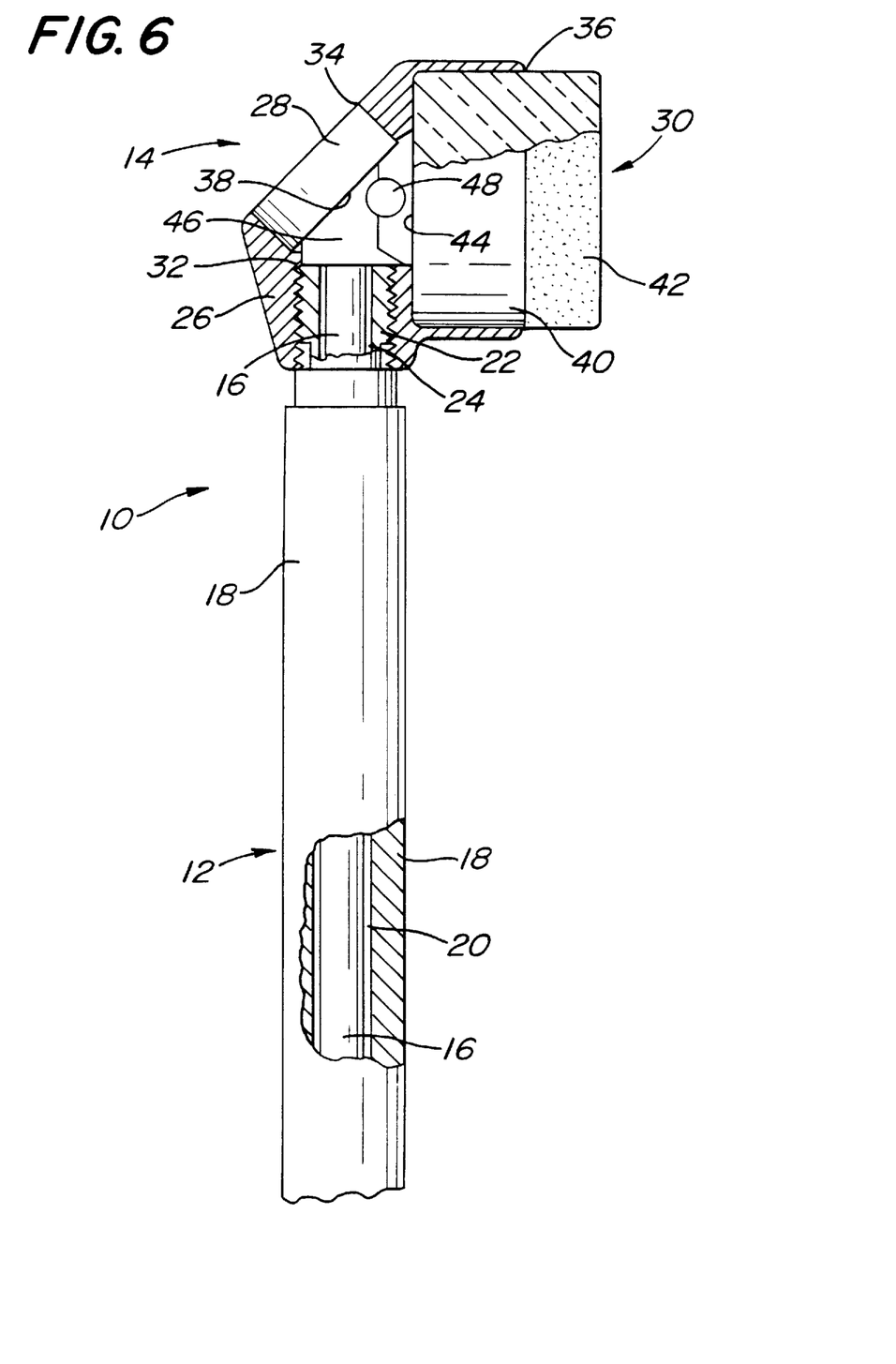
FIG. 6 is a side view, partially in section, of a laser energy delivery device including a transverse laser probe according to another embodiment of the present invention.

By canting the device 10 off the longitudinal axis of the energy delivery system, the surgeon can better observe the progress of the to and fro, transverse and the sweeping movements. This is illustrated in FIG. 5B, which schematically represents a "surgeon's eye view" of the TURP procedure just described. This is the view the surgeon would see through the endoscope, looking toward the bladder orifice. As FIG. 5B illustrates, the jut or lateral extension of the tissue contact portion of tip member 14 is readily visible to the surgeon, permitting immediate visual observation of the progress of the ablation and confirmation that the tissue contact surface of tip member 14 is working within anatomical landmarks.

The present invention may be embodied in other specific forms without departing from the spirit or essential attributes thereof and, accordingly, reference should be made to the appended claims, rather than to the foregoing specification, as indicating the scope of the invention.

We claim:

1. A laser medical device for delivering energy to tissue to be treated, comprising a laser energy transmitting conduit having a longitudinal axis and having a proximal end for connection to a source of laser energy and a distal end from which laser energy transmitted by the conduit is emitted, a laser energy redirecting member adjacent the distal end of the conduit for redirecting the laser energy in a lateral direction with respect to the axis of the conduit, and a tissue contact member adjacent the laser energy redirecting member and having a longitudinal axis generally transverse to the axis of the conduit and further having an input surface for receiving laser energy redirected by the laser energy redirecting member and transmitting the laser energy received from the laser energy redirecting member, the tissue contact member terminating in a tissue contact surface having a radius of curvature, the dimensions of the tissue contact member and the radius of curvature of the tissue contact surface are of a structure such that laser energy is transmitted divergently therethrough and impinges upon the tissue contact surface in a substantially diffuse pattern.

2. A laser medical device as in claim 1, wherein the tissue contact member has a longitudinal cross section, the longitudinal cross section having an average dimension and said radius of curvature being not less than one-half said average dimension.

3. A laser medical device as in claim 1, wherein the tissue contact member is substantially in the shape of a right circular cylinder, and a radius of curvature not less that one-half the diameter of the cylinder.

4. A laser medical device as in claim 1, wherein the radius of curvature of the tissue contact surface is infinite.

5. A laser medical device as in claim 1, wherein the laser energy redirecting member is a reflector.

6. A laser medical device as in claim 1, wherein the laser energy redirecting member is a refractive prism.

7. A laser medical device as in claim 1, wherein the tissue contact member comprises a body portion in substantially the shape of a right cylinder, one end thereof being a laser energy input end and the other end being the tissue contact surface, the body portion having a diameter greater than its longitudinal dimension, and wherein the tissue contact surface is a portion of a sphere surface.

8. A laser medical device as in claim 1, wherein the longitudinal axis of the tissue contact member is at an angle of substantially 90° to the axis of the conduit.

9. A laser medical device as in claim 1, wherein the longitudinal axis of the tissue contact member is at an angle of less than 90° to the axis of the conduit.

10. A laser medical device as in claim 1, wherein the longitudinal axis of the tissue contact member is at an angle of greater than 90° to the axis of the conduit.

11. A laser medical device as in claim 1, wherein the surface of the tissue contact member is treated to partially absorb laser energy and convert the absorbed energy to thermal energy.

12. A laser medical device as in claim 1, wherein the tissue contact surface is spaced a preselected distance from the longitudinal axis of the laser energy transmitting conduit.

13. A laser medical device as in claim 1, wherein the shape and dimensions of the tissue contact member are chosen to cause laser energy to propagate therethrough without undergoing internal reflection.

* * * * *

UNITED STATES PATENT AND TRADEMARK OFFICE
CERTIFICATE OF CORRECTION

PATENT NO. : 5,833,683
DATED : November 10, 1998
INVENTOR(S) : Fuller et al.

It is certified that error appears in the above-identified patent and that said Letters Patent is hereby corrected as shown below:

On page 2 under U.S. PATENT DOCUMENTS 4,694,828 delete - - Eichenbaru - - and insert "Eichenbaurn - -;

On page 2 under OTHER PUBLICATIONS second publication delete - - Hashimotyo - - and insert "Hashimoto";

On page 2 under OTHER PUBLICATIONS last publication delete - - Ultrasonice - - and insert "Ultrasonic";

Col. 2 line 67 delete - - directional - - and insert "direction";

Col. 3 line 49 delete - - character - - and insert "characteristically";

Col. 4, line 30 delete - - selection - - and insert "selections";

Col. 5 line 41 delete - - hemostatis - - and insert "hemostasis";

Col. 5 line 43 delete - - irridiated - - and insert "irradiated";

Col. 6 line 52 delete - - with - - and insert "the";

Col. 10 line 40 delete - - optic - -;

Col. 11 line 35 delete - - may 30 - - and insert "30 may";

UNITED STATES PATENT AND TRADEMARK OFFICE
CERTIFICATE OF CORRECTION

PATENT NO. : 5,833,683
DATED : November 10, 1998
INVENTOR(S) : Fuller et al.

It is certified that error appears in the above-identified patent and that said Letters Patent is hereby corrected as shown below:

Col. 12 line 60 after portion insert "40";

Col. 14 line 48 after beam delete - -, - -;

Col. 14 line 49 after element delete - -, - - and insert "or";

Col. 16 line 12 after the word "and" insert - - arc - -;

Col. 17 line 57 delete - - lumenal - - and insert "luminal";

Col. 17 line 59 delete - - lumenal - - and insert "luminal";

Col. 18, line 35 delete - - clock - - and insert "clockwise";

Signed and Sealed this

Fifteenth Day of June, 1999

Attest:

Q. TODD DICKINSON

*Attesting Officer*    *Acting Commissioner of Patents and Trademarks*